United States Patent
Sakairi et al.

(10) Patent No.: US 11,655,395 B2
(45) Date of Patent: May 23, 2023

(54) SUPPORT FILM FOR TAPE MATERIAL, AND TAPE MATERIAL

(71) Applicants: TOPPAN PRINTING CO., LTD., Tokyo (JP); HISAMITSU PHARMACEUTICAL CO., INC., Tosu (JP)

(72) Inventors: Koji Sakairi, Tokyo (JP); Atsushi Matsushima, Tokyo (JP); Tomohiro Shinoda, Tsukuba (JP); Atsushi Sonobe, Tsukuba (JP)

(73) Assignees: TOPPAN PRINTING CO., LTD., Tokyo (JP); HISAMITSU PHARMACEUTICAL CO., INC., Tosu (JP)

( * ) Notice: Subject to any disclaimer, the term of this patent is extended or adjusted under 35 U.S.C. 154(b) by 22 days.

(21) Appl. No.: 16/263,525

(22) Filed: Jan. 31, 2019

(65) Prior Publication Data
US 2019/0161647 A1    May 30, 2019

Related U.S. Application Data

(63) Continuation of application No. PCT/JP2017/027993, filed on Aug. 2, 2017.

(30) Foreign Application Priority Data

Aug. 4, 2016   (JP) .................. JP2016-153931

(51) Int. Cl.
  *C09J 7/29*    (2018.01)
  *C09J 201/02*  (2006.01)
(Continued)

(52) U.S. Cl.
  CPC .............. *C09J 7/29* (2018.01); *B32B 27/40* (2013.01); *C09J 201/00* (2013.01); *C09J 201/02* (2013.01);
(Continued)

(58) Field of Classification Search
  CPC ............ C09J 7/29; C09J 201/00; B32B 27/40
  See application file for complete search history.

(56) References Cited

U.S. PATENT DOCUMENTS

| | | | |
|---|---|---|---|
| 2004/0009357 A1* | 1/2004 | Kusudou | C08F 8/12 428/480 |
| 2004/0054069 A1* | 3/2004 | Kusudou | C08F 8/12 524/557 |

(Continued)

FOREIGN PATENT DOCUMENTS

| CN | 1878836 A | 12/2006 |
|---|---|---|
| CN | 101191032 A | 6/2008 |

(Continued)

OTHER PUBLICATIONS

"Method for testing moisture permeability of moisture-proof packaging materials (Cup method)" Japanese Industrial Standards, JIS Z0208, 1976, 12 pages.

(Continued)

*Primary Examiner* — Scott R. Walshon
*Assistant Examiner* — Thomas A Mangohig
(74) *Attorney, Agent, or Firm* — Sughrue Mion, PLLC

(57) ABSTRACT

A support film for a tape material, includes a film-shaped support formed of polyurethane; and a barrier layer containing an aromatic isocyanate-based polyurethane and a layered inorganic compound and formed on one surface of the support.

10 Claims, 4 Drawing Sheets

(51) Int. Cl.
  *B32B 27/40* (2006.01)
  *C09J 201/00* (2006.01)
(52) U.S. Cl.
  CPC ...... *C09J 2301/162* (2020.08); *C09J 2400/12* (2013.01); *C09J 2471/001* (2013.01); *C09J 2475/001* (2013.01); *C09J 2475/006* (2013.01)

(56) References Cited

U.S. PATENT DOCUMENTS

| | | | |
|---|---|---|---|
| 2005/0084686 | A1 | 4/2005 | Imaizumi |
| 2007/0231571 | A1* | 10/2007 | Lane ........................... C09J 7/38 428/354 |
| 2008/0070043 | A1* | 3/2008 | Arai ................... C08G 18/3206 428/425.8 |
| 2012/0238446 | A1 | 9/2012 | Tsuchimura et al. |
| 2013/0183522 | A1 | 7/2013 | Takada et al. |
| 2013/0209799 | A1 | 8/2013 | Takada et al. |
| 2014/0329950 | A1* | 11/2014 | Shimoguchi ............ B32B 27/34 524/403 |
| 2014/0370270 | A1 | 12/2014 | Kaminaga et al. |
| 2015/0183989 | A1* | 7/2015 | Manitiu .................. B29D 23/00 525/66 |
| 2016/0040035 | A1* | 2/2016 | Omura .................. B32B 15/082 428/324 |

FOREIGN PATENT DOCUMENTS

| | | |
|---|---|---|
| CN | 103562248 A | 2/2014 |
| EP | 1 081 170 A2 | 3/2001 |
| EP | 2 799 229 A1 | 11/2014 |
| EP | 2 990 451 A1 | 3/2016 |
| EP | 3483229 A1 | 5/2019 |
| JP | 04-035935 A | 2/1992 |
| JP | 09-151265 A | 6/1997 |
| JP | 2001-098047 A | 4/2001 |
| JP | 2001-98047 A | 4/2001 |
| JP | 2003-285389 A | 10/2003 |
| JP | 2005-138581 A | 6/2005 |
| JP | 2005-220154 A | 8/2005 |
| JP | 2008-297527 A | 12/2008 |
| JP | 2012-210805 A | 11/2012 |
| JP | 2014-214232 A | 11/2014 |
| JP | 2015-044396 A | 3/2015 |
| JP | 2015-104831 A | 6/2015 |
| JP | 2016-013993 A | 1/2016 |
| JP | 2018-177737 A | 11/2018 |
| TW | 201208876 A | 3/2012 |
| TW | 201512331 A | 4/2015 |
| WO | 2012/014585 A1 | 2/2012 |
| WO | 2012/014587 A1 | 2/2012 |
| WO | 2013/111773 A1 | 8/2013 |
| WO | 2015/016069 A1 | 2/2015 |

OTHER PUBLICATIONS

International Search Report for PCT/JP2017/027993, dated Sep. 19, 2017.
Communication dated Feb. 10, 2020 from the European Patent Office in application No. 17837000.3.
"Method for testing moisture permeability of moisture-proof packaging materials (Cup method)" Japanese Industrial Standards, JIS Z0208, 1979, 12 pages.
Communication dated Nov. 20, 2020 from the Taiwanese (TW) Patent Office in Application No. 106126010.
Communication dated Aug. 31, 2020, issued by the State Intellectual Property Office of the P.R.C. in application No. 201780047637.8.
Yuhan Wu, "Review of Patents in the Field of EVOH Packaging Materials", Chemical Enterprise Management, vol. 19, Jul. 1, 2016, p. 108.
Notice of Allowance dated Aug. 24, 2021 from the Japanese Patent Office in JP Application No. 2018-531944.

* cited by examiner

SUPPORT FILM FOR TAPE MATERIAL, AND TAPE MATERIAL

CROSS REFERENCE TO RELATED APPLICATIONS

This application is a continuation application based on a PCT Patent Application No. PCT/JP2017/027993, filed Aug. 2, 2017, whose priority is claimed on Japanese Patent Application No. 2016-153931, filed on Aug. 4, 2016, the contents of which are hereby incorporated by reference.

BACKGROUND OF THE INVENTION

Field of the Invention

The present invention relates to a support film for a tape material and a tape material using the support film.

Description of Related Art

A tape material in which an adhesive layer is formed on one surface of a sheet-shaped or film-shaped support is widely used for various uses such as medical or industrial uses. The adhesive layer of such a tape material is mixed with a plasticizer in addition to an adhesive in some cases. Since it is considered that, depending on the material of the support, the plasticizer is adsorbed and thus effects of the tape material cannot be exhibited, plasticizer barrier properties are preferably imparted in at least a surface in contact with the adhesive layer in the support.

As a film material having plasticizer barrier properties, a support film for a tape material having a barrier layer disclosed in Patent Document 1 (Pamphlet of PCT International Publication No. WO2012/014585), Patent Document 2 (Pamphlet of PCT International Publication No. WO2012/014587), and Patent Document 3 (Pamphlet of PCT International Publication No. WO2013/111773) is known. The support film for a tape material is provided with a barrier layer obtained by applying a barrier coating agent, in which montmorillonite, which is a layered inorganic compound, and polyvinyl alcohol which is a water-soluble polymer, are mixed with each other on one surface of a film-shaped support formed of polyurethane.

In the support film for a tape material disclosed in the patent documents, a barrier layer, which can favorably maintain plasticizer barrier properties even in a case where the support film for a tape material is elongated, is formed on a support.

For example, if water vapor barrier properties of a support film for a tape material are improved in a patch in which an adhesive containing a drug is used on an adhesive layer, an effect of occlusive dressing therapy (ODT) becomes high, and an absorption rate of the drug into the skin can be enhanced. In addition, other various uses are considered.

In a case where a rubber material is used in the adhesive, water vapor barrier properties of the rubber material itself are high, and water vapor barrier properties are not required in the support film for a tape material. However, in a case where an acrylic material or silicone material is used in the adhesive, water vapor barrier properties are lower than those of the rubber material, and water vapor barrier properties are required in the barrier layer of the support film for a tape material in order to enhance the effects of ODT and the like.

On the other hand, the plasticizer barrier properties described above are also required in the barrier layer.

SUMMARY OF THE INVENTION

The present invention is made in view of the above circumstances, and an object of the present invention is to provide a support film for a tape material and a tape material that can favorably maintain plasticizer barrier properties and water vapor barrier properties.

A support film for a tape material according to a first aspect of the present invention includes a film-shaped support formed of polyurethane; and a barrier layer containing an aromatic isocyanate-based polyurethane and a layered inorganic compound and formed on one surface of the support.

The barrier layer may further contain a polyhydric alcohol.

A tape material according to a second aspect of the present invention includes the support film for a tape material according to the aspect and an adhesive layer formed on the barrier layer.

According to the support film for a tape material and the tape material according to the aspects of the present invention, it is possible to favorably maintain water vapor barrier properties while retaining plasticizer barrier properties.

DETAILED DESCRIPTION OF THE INVENTION

Hereinafter, the tape material according to the first embodiment of the present invention will be described with reference to FIGS. 1 to 7.

The tape material according to the present embodiment is formed to include a support film for a tape material (hereinafter, simply referred to as "support film") according to the present embodiment, and can be used as an adhesive tape and the like in various fields such as for industrial use, for packaging use, for protective use, for labeling use, for masking use, for sanitary material such as paper diapers, for medical use such as sticking plaster and transdermal administration, for cosmetic use, and for domestic use.

Figure 1:
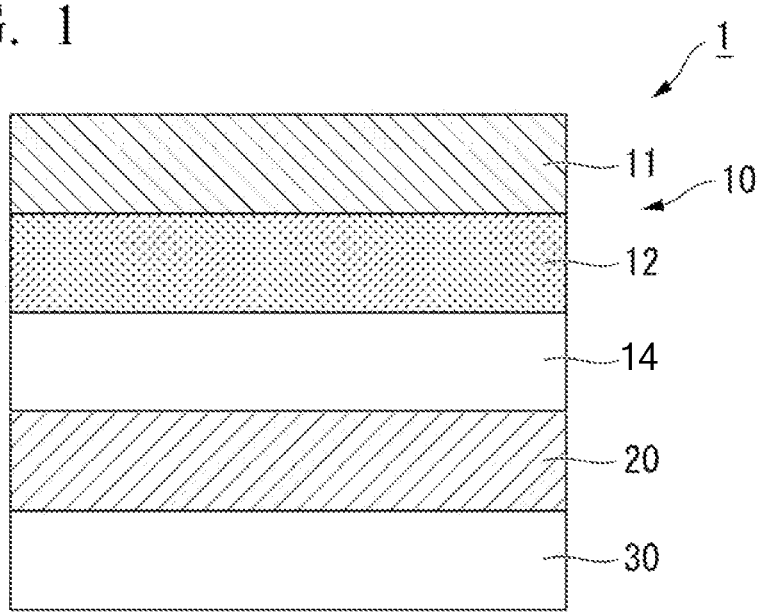
FIG. 1 is a sectional view of a tape material according to a first embodiment of the present invention in a thickness direction.

FIG. 1 is a sectional view of a tape material 1 according to the present embodiment in a thickness direction. The tape material 1 includes a support film 10, an adhesive layer 20 formed on one surface of the support film 10, and a release member 30 covering the adhesive layer.

The support film 10 includes a support 11 containing polyurethane and formed in a film shape and a barrier layer 12 formed on one surface of the support 11.

In the support 11, polyurethane having flexibility is formed in a film shape. In the present embodiment, polyurethane forming the support 11 is not particularly limited, materials used in the conventional polyurethane film can be used, and can be appropriately used depending on the use. Examples thereof include polyether-based polyurethane, polyester-based polyurethane, polycarbonate-based polyurethane, and the like. For use requiring water resistance, polyether-based polyurethane or polycarbonate-based polyurethane is preferable.

In addition, the type of isocyanate forming a urethane bond, the yellowing type, the non-yellowing type, or the like is not limited to a specific polyurethane, and can be appropriately selected depending on the use, the storage period or method when used, the type of used plasticizer, and the like.

The barrier layer 12 contains polyurethane and a layered inorganic compound and is formed on one surface of the support 11. As the polyurethane, polyurethane of a water-based material which is coatable to the support 11 containing polyurethane having low resistance with respect to a solvent or a plasticizer, is used. Among the water-based polyurethane, water-based polyurethane of gas barrier type (having gas barrier properties) is appropriate from the viewpoint of plasticizer barrier properties and water vapor barrier properties, and aromatic isocyanate-based polyurethane is particularly appropriate. The aromatic isocyanate-based polyurethane is polyurethane formed of isocyanate including an aromatic group on a main chain or side chain and polyol. At this time, the isocyanate including an aromatic group on a main chain or a side chain may form a part or the entirety of isocyanate forming aromatic isocyanate-based polyurethane. The aromatic isocyanate-based polyurethane can form a dense film.

As the layered inorganic compound, synthetic mica is preferable. In addition, montmorillonite or kaolinite, vermiculite, mica, and the like can be used. It is considered that the layered inorganic compound exhibits water vapor barrier properties due to a labyrinthine effect by laminating a layered inorganic compound having a flat structure when forming the barrier layer 12. A layered inorganic compound having a large particle diameter and a large aspect ratio is preferable for enhancing water vapor barrier properties.

In addition, by using an aromatic isocyanate-based polyurethane in which the layered inorganic compound is added to the barrier layer 12, it is possible to improve plasticizer barrier properties and water vapor barrier properties.

In the layered inorganic compound used in the barrier layer 12 according to the present embodiment, it is preferable that an average particle diameter be 0.1 μm or greater and an aspect ratio be 100 or greater.

In addition, in the layered inorganic compound used in the barrier layer 12, it is more preferable that an average particle diameter be 3 μm or greater and an aspect ratio be 100 or greater.

In the present embodiment, the average particle diameter and the aspect ratio are measured by using a laser diffraction-scattering-type particle diameter distribution measurement device.

The barrier layer 12 is formed of a coating film constituted of a mixture of an aromatic isocyanate-base polyurethane and a layered inorganic compound, and if cracks occur at the time of elongation of the tape material 1, plasticizer barrier properties and water vapor barrier properties are deteriorated. In order to prevent the occurrence of cracks of the barrier layer 12 at the time of elongation of the tape material 1, a polyhydric alcohol is preferably added to the barrier layer 12. As the polyhydric alcohol, glycerin, ethylene glycol, propylene glycol, polyethylene glycol, and the like can be used. Among these, glycerin can be appropriately used. In order to impart elongation resistance to the barrier layer 12, it is preferable to increase an addition amount of the polyhydric alcohol in the barrier layer 12.

On the other hand, in a case where the addition amount of the polyhydric alcohol in the barrier layer 12 is increased, water vapor barrier properties tend to be deteriorated. Desired elongation resistance or water vapor barrier properties vary by use aspects of the tape material, but the addition amount of the a polyhydric alcohol is preferably within a range of equal to or more than 5 wt % and equal to or less than 30 wt % with respect to a total amount (100 wt %) of an aromatic isocyanate-based polyurethane and a layered inorganic compound.

The adhesive layer 20 is formed by mixing a plasticizer with an adhesive base material, and is formed on the barrier layer 12 by being applied on a surface opposite to the surface provided with the support 11. In other words, the tape material 1 includes an adhesive layer 20 formed on the barrier layer 12 in the support film 10 for a tape material.

The adhesive used in the adhesive layer 20 is not particularly limited. As the adhesive, rubber-based polymer such as natural rubber, synthetic isoprene rubber, reclaimed rubber, styrene butadiene rubber (SBR), styrene-isoprene-styrene block copolymer (SIS), styrene-butadiene-styrene block copolymer (SBS), polyisobutylene, SEBS, and SEPS, acrylic polymer such as (meth)acrylic ester copolymer having (meth)acrylic esters as main monomers, silicone-based polymer such as silicone rubber, silicone resin, dimethyl siloxane, and diphenyl siloxane, and various materials such as polyvinyl ether-based material, polyvinyl ester-based material, EVA-based material, and polyester-based material can be used.

The plasticizer is not particularly limited, and various plasticizers such as petroleum-based oil (paraffin-based process oil, naphthenic process oil, aromatic process oil, and the like), dibasic acid ester (dibutyl phthalate, dioctyl phthalate, and the like), liquid rubber (polybutene, liquid isoprene, liquid polyisobutylene, and the like), vegetable oil-based (castor oil, tall oil, and the like), liquid fatty acid esters (isopropyl myristate, laurate hexyl, diethyl sebacate, sebacic acid diisopropyl, and the like), triacetin, sorbitan fatty acid esters, sucrose fatty acid esters, fatty acid glycerin esters, surfactants, and the like can be used.

In addition, various tackifiers may be mixed to enhance adhesion. For example, rosin-based resin such as rosin, modified rosin, rosin ester, and the like, terpene-based resin such as terpene resin, aromatically modified terpene resin, hydrogenated terpene resin, terpene phenol resin, and the like, petroleum resin such as aliphatic petroleum resin, aromatic petroleum resin, copolymeric petroleum resin, hydrogenated petroleum resin, DCPD-based petroleum resin, and the like, styrene-based resin, substituted styrene-based resin, xylene resin, phenol-based resin, chroman indene resin, and the like can be exemplified.

In addition, depending on the use of the tape material, an anti-oxidant, a filler, a cross-linking agent, an ultraviolet-absorbing agent, a colorant, a flame retardant, a conducting agent, a foaming agent, and the like may be added thereto.

In a case where the support film 10 is used in a patch including a drug on the adhesive layer 20, it is appropriately prevent the drug from reaching the support 11 by the barrier layer 12.

The release member 30 is a member that protects an adhesive surface of the adhesive layer 20 until pasting of the tape material 1 to a subject, and various types of known release paper and the like can be appropriately used. In a case where the tape material 1 is wound around a core material in a roll shape, the release member 30 may not necessarily be provided.

Figure 2:
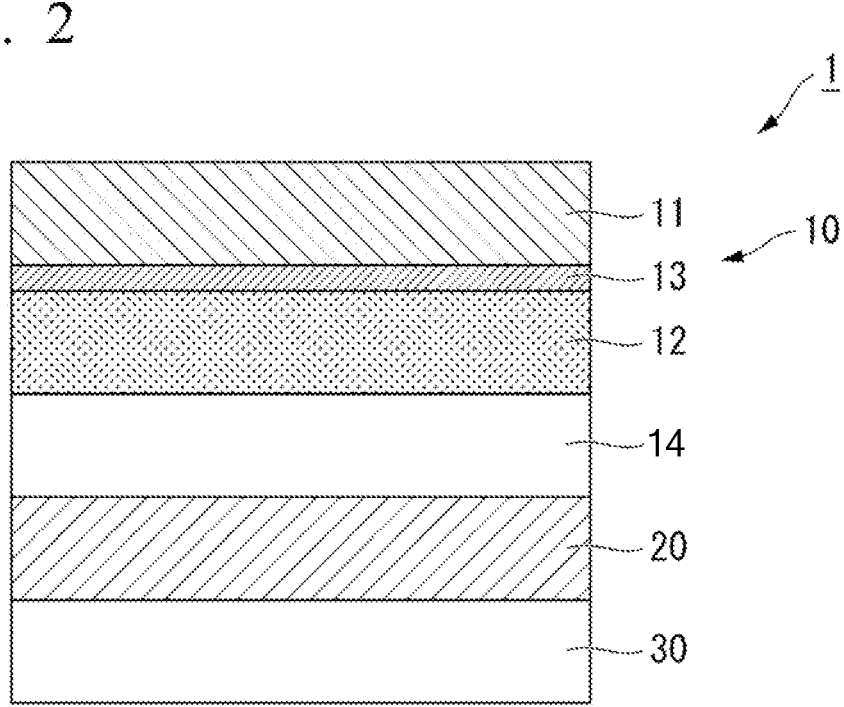
FIG. 2 is a sectional view of a modification example of the tape material according to the first embodiment of the present invention in the thickness direction.

As shown in FIG. 2, the support film 10 may form an undercoat layer 13 between the support 11 and the barrier layer 12. The undercoat layer 13 can be used for various uses. For example, a layer on which a pattern or the like is printed can be formed as the undercoat layer 13, and can be used for adding a pattern or letter to the support film 10. The undercoat layer 13 may be entirely formed between the support 11 and the barrier layer 12, and may be formed in a pattern shape. An aqueous ink and the like can be used in formation of the undercoat layer 13.

Next, a method for producing the support film 10 will be described.

First, a support 11 formed of polyurethane is prepared (support preparation step). Next, a barrier layer coating liquid is applied on one surface of the support 11, and dried to form a barrier layer 12 (barrier layer formation step). The barrier layer coating liquid contains aromatic isocyanate-based polyurethane and a layered inorganic compound, and water is used as a dispersion medium. In addition, the barrier layer coating liquid can preferably contain polyhydric alcohol such as glycerin. In addition, various additives such as emulsifier and dispersant may be further contained in the barrier layer coating liquid. In addition, as the dispersion medium, alcohol and the like other than water may be contained.

In the above manner, the support film 10 according to the present embodiment is completed.

In the production method according to the present embodiment, an undercoat layer formation step of forming the undercoat layer 13 may be further provided between the support preparation step and the barrier layer formation step.

Next, experiments and experiment results in relation to the effect of each layer in the support film 10 will be described.

(Experiment 1 Examination of Polyurethane Used in Barrier Layer)

(1-1 Sample Preparation)

As candidates of polyurethane used in the barrier layer, three types of an aromatic isocyanate-based polyurethane, which is a water-based polyurethane having gas barrier properties, a polyester-based urethane-modified polyol, and a self-cross-linking polyurethane containing a silanol group in the skeleton were selected.

As the water-based polyurethane having gas barrier properties, two types of samples of Sample I and Sample II were prepared. Both of Sample I and Sample II are water-based polyurethane having gas barrier properties, but each has a different composition. As the polyester-based urethane-modified polyol, three types of samples of Sample III to Sample V were prepared. All of Sample III to Sample V are polyurethane obtained by using polyester-based urethane-modified polyol, and are not aromatic isocyanate-based polyurethane. In addition, each sample of Sample III to Sample V has a different composition. As the self-cross-linking polyurethane containing a silanol group in the skeleton, two types of samples of Sample VI and Sample VII were prepared. Sample VI and Sample VII are self-cross-linking polyurethane containing a silanol group in the skeleton, and are not aromatic isocyanate-based polyurethane. In addition, each of Sample VI and Sample VII has a different composition.

In addition, as the barrier layer, two types of a barrier layer of a single polyurethane layer and a barrier layer formed of polyurethane to which 10 wt % of synthetic mica was added were prepared. The barrier layer formed of polyurethane to which 10 wt % of synthetic mica was added is a barrier layer including 10 wt % of synthetic mica and 90 wt % of polyurethane (solid content).

The barrier layer 12 was applied and formed on the support such that a solid content of coating liquid was 2.0 g/m$^2$.

As the support 11, a polyether-based polyurethane support having a thickness of 20 μm was used. As the synthetic mica, a synthetic mica having an average particle diameter of 11 μm and an aspect ratio of 1000 or greater was used.

In Experiment 1 and the following experiments, a method for measuring an average particle diameter and an aspect ratio of synthetic mica, colloidal silica, montmorillonite, and the like uses a laser diffraction scattering particle diameter distribution measurement device.

Using the samples, two types of evaluations of plasticizer barrier evaluation and water vapor barrier properties evaluation were performed. The two types of evaluations were independently performed by using different evaluation pieces.

(1-2 Experiment Procedure)

Figure 3:
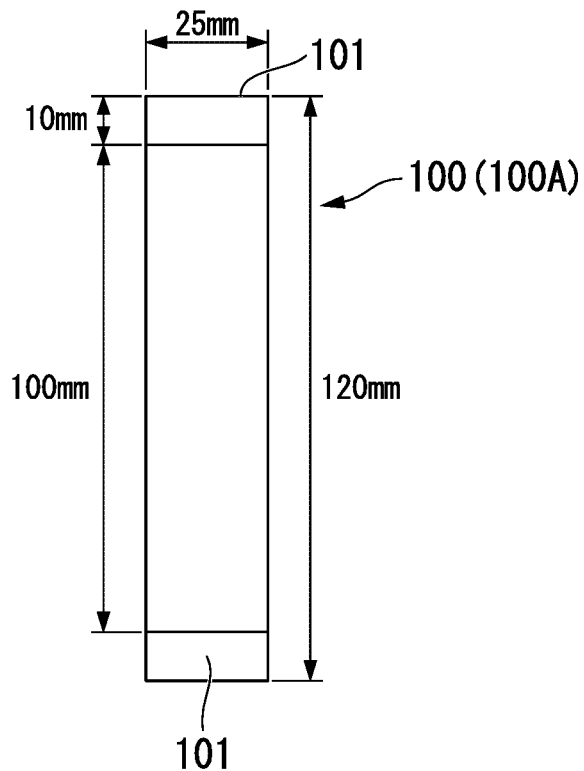
FIG. 3 is a view showing a procedure of an experiment examining plasticizer barrier properties of a barrier layer.

In the plasticizer barrier evaluation, three types of prepared samples 100 were cut in a size of 25 mm×120 mm as shown in FIG. 3, and a sample piece 100A was disposed such that a barrier layer was on an upper side on a black acrylic plate in which scales were described, and an end of the sample piece 100A was fixed with an adhesive tape 101. Next, without performing elongation with respect to the evaluation piece 100A, the other end of the evaluation piece 100A was fixed on the black acrylic plate with the adhesive tape 101. A dimension (length) of a portion not covered with the adhesive tape 101 in a longitudinal direction was 100 mm.

Figure 4:
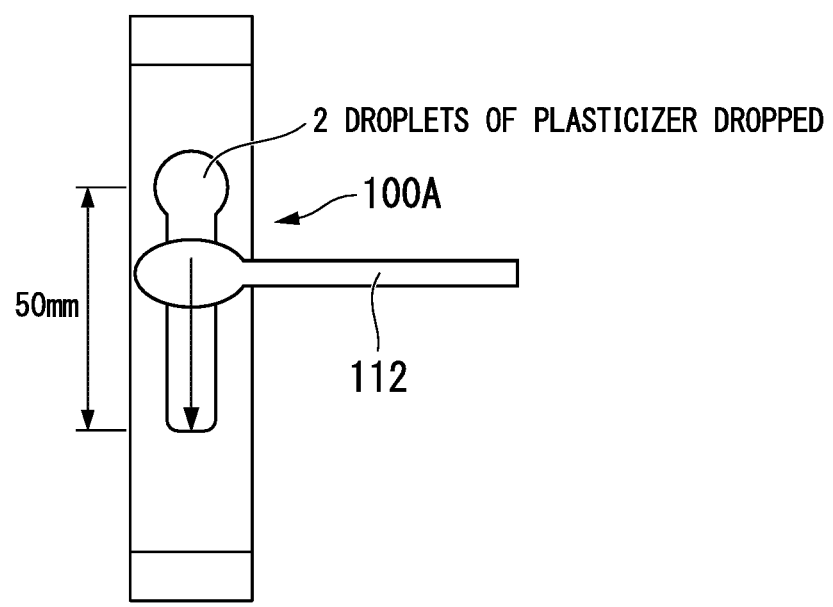
FIG. 4 is a view showing a procedure of an experiment examining plasticizer barrier properties of the barrier layer.

After attachment of each evaluation piece 100A to the acrylic plate, as shown in FIG. 4, two droplets (approximately 0.08 g) of a plasticizer were dropped on the evaluation piece 100A with a pipette, and the dropped plasticizer was spread to a length of 50 mm on the evaluation piece 100A by using a cotton swab 112. As the plasticizer, isopropyl myristate (IPM) was used. The plasticizer was wiped after being left for 30 minutes and after being left for 3 hours at room temperature, and a swelling degree of the support 11 was visually evaluated. As an index, presence or absence of wrinkles in the support 11 caused by swelling was used (2-stage evaluation: wrinkles due to swelling were not acknowledged: A, and wrinkles due to swelling were acknowledged: B).

In the water vapor barrier properties evaluation, measurement of a water vapor permeability rate (WVTR) was performed by "testing methods for determination of the water vapor transmission rate of moisture-proof packaging materials (dish method)" of JIS-Z0208 (1976).

Measurement was performed after standing still for 3 hours at 40° C. and 90% RH (relative humidity) by the dish method using a jig having an opening diameter of 80 mm, and the measurement value was converted into a moisture permeability amount for 24 hours per 1 m$^2$ to obtain a water vapor permeability rate.

(1-3 Result)

The result is shown in Table 1. As a result of evaluating plasticizer barrier properties, favorable characteristics were obtained in the aromatic isocyanate-based polyurethane, which is a water-based polyurethane having gas barrier properties.

In the water vapor barrier properties evaluation as well, favorable characteristics were obtained in the aromatic isocyanate-based polyurethane, which is a water-based polyurethane having gas barrier properties. In particular, it was shown that by adding 10 wt % of synthetic mica, which is a layered inorganic compound, to the layer, a further lower water vapor permeability rate can be maintained, and high water vapor barrier properties are exhibited.

From the above result, it was determined that by forming a barrier layer 12 with a mixture of the aromatic isocyanate-based polyurethane, which is a water-based polyurethane having gas barrier properties, and a synthetic mica, which is a layered inorganic compound, it is possible to obtain plasticizer barrier properties and water vapor barrier properties.

The result of the plasticizer barrier properties (no elongation) described in Table 1 is a result of evaluation after being left for 3 hours.

As the support 11, a polyether-based polyurethane support having a thickness of 20 μm was used.

(2-2 Experiment Procedure)

An experiment procedure of water vapor barrier properties is the same as that of Experiment 1.

(2-3 Result)

Figure 5:
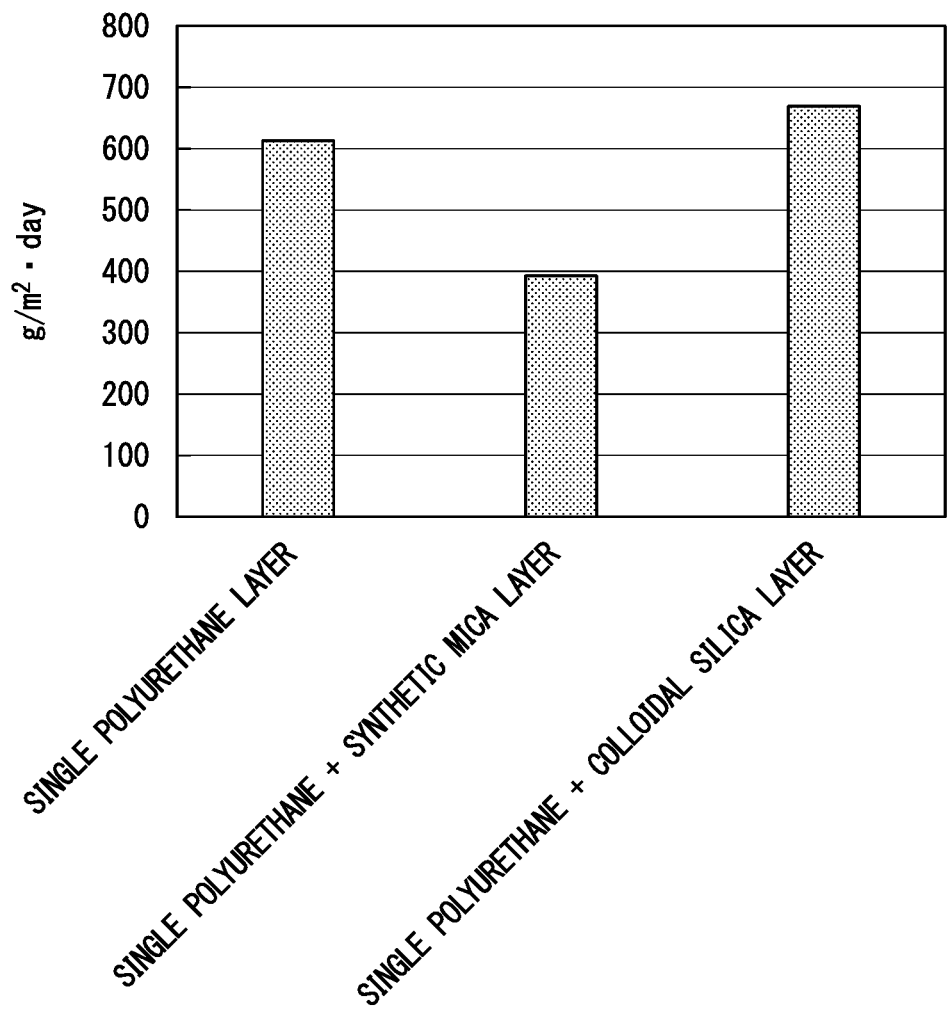
FIG. 5 is a graph showing a relationship between a type of a layered inorganic compound and a water vapor permeability rate.

The result is shown in FIG. 5. The ordinate axis of the graph of FIG. 5 shows a water vapor permeability rate. In the barrier layer using a spherical mineral such as colloidal silica, the effect of improving water vapor barrier properties was small, and in the barrier layer using synthetic mica, the effect of improving water vapor barrier properties was determined. Table 2 shows average particle diameters and aspect ratios of the used synthetic mica and colloidal silica. It is considered that the synthetic mica has better water vapor barrier properties than the colloidal silica since the water vapor barrier properties are affected by a difference in aspect ratios. In addition, it is considered that the water vapor barrier properties were also affected by the average particle diameter, and the one having a large average particle diameter had favorable water vapor barrier properties. It is considered that labyrinthine effect due to a layered inorganic compound such as a synthetic mica contributes to the result.

TABLE 1

| | | | WATER VAPOR PERMEABILITY RATE (g/m² per day) | |
|---|---|---|---|---|
| | | PLASTICIZER BARRIER EVALUATION (NO ELONGATION) | SINGLE LAYER (NO SYNTHETIC MICA) | ADDITION OF 10% OF SYNTHETIC MICA IN LAYER |
| I | WATER-BASED | A | 550 | 217 |
| II | POLYURETHANE HAVING GAS BARRIER PROPERTIES | A | 607 | 302 |
| III | POLYESTER-BASED | B | 649 | 638 |
| IV | URETHANE- | B | 611 | 678 |
| V | MODIFIED POLYOL | B | 632 | 519 |
| VI | SELF-CROSS-LINKING | B | 628 | 550 |
| VII | POLYURETHANE CONTAINING A SILANOL GROUP IN SKELETON | B | 590 | 489 |

Next, an experiment was performed to evaluate water vapor barrier properties due to the type of the layered inorganic compound contained in the barrier layer 12 and the experiment result will be described.

(Experiment 2 Examination in Relation to Layered Inorganic Compound)

(2-1 Sample Preparation)

As a barrier layer on a support, three types of samples of a single polyurethane layer not containing a layered inorganic compound, a barrier layer formed of polyurethane to which 15 wt % of synthetic mica was added, and a barrier layer formed of polyurethane to which 15 wt % of colloidal silica was added were prepared. Here, the barrier layer formed of polyurethane to which 15 wt % of synthetic mica was added is a barrier layer formed such that the synthetic mica is 15 wt % and polyurethane is 85 wt % (solid content). In addition, the barrier layer formed of polyurethane to which 15 wt % of colloidal silica was added is a barrier layer formed such that the colloidal silica is 15 wt % and polyurethane is 85 wt % (solid content).

The barrier layers were applied and formed on the support such that the solid content of a coating liquid was 2.0 g/m².

Therefore, it is considered that besides the synthetic mica, natural mica and montmorillonite which are a layered inorganic compound, and the like can be also appropriately used.

TABLE 2

| | AVERAGE PARTICLE DIAMETER (μm) | ASPECT RATIO |
|---|---|---|
| SYNTHETIC MICA | 11 | 1000< |
| COLLOIDAL SILICA | 0.2 | 1 |

Next, the experiment result in which elongation resistance of the barrier layer 12 due to polyhydric alcohol was examined is shown.

(Experiment 3 Examination of Elongation Resistance Imparting Effect of Barrier Layer Due to Polyhydric Alcohol)

(3-1 Sample Preparation)

A sample of polyurethane containing 10 wt % of synthetic mica without adding glycerin was prepared as a reference (referred to as Control in the table), and samples of Samples 1A containing 10 wt % of synthetic mica, Samples 2A containing 15 wt % of synthetic mica, and Samples 3A containing 20 wt % of synthetic mica were prepared. Three types of variation samples in which a content ratio (wt %) of glycerin was changed in respective Samples 1A to 3A were prepared. Here, Control is a sample in which 10 wt % of synthetic mica and 90 wt % of polyurethane were formed on a barrier layer 12. Samples 1A are samples obtained by adding glycerin such that a proportion of glycerin is 5 wt % to 12.5 wt % with respect to 10 wt % of synthetic mica and 90 wt % of polyurethane (a total of 100 wt %) to form a barrier layer 12. Samples 2A are samples obtained by adding glycerin such that a proportion of glycerin is 10 wt % to 15 wt % with respect to 15 wt % of synthetic mica and 85 wt % of polyurethane (a total of 100 wt %) to form a barrier layer 12. Samples 3A are samples obtained by adding glycerin such that a proportion of glycerin is 10 wt % to 15 wt % with respect to 20 wt % of synthetic mica and 80 wt % of polyurethane (a total of 100 wt %) to form a barrier layer 12.

The barrier layer 12 was applied and formed on a support such that a solid content of a coating liquid was 2.0 g/m$^2$.

As the support 11, a polyether-based polyurethane support having a thickness of 20 μm was used. As the synthetic mica, a synthetic mica having an average particle diameter of 11 μm and an aspect ratio of 1000 or greater was used.

On the barrier layer, an overcoat layer 14 constituted of 80 wt % of polyvinyl alcohol and 20 wt % of titanium lactate is formed. By using the overcoat layer 14 along with the barrier layer 12, water vapor barrier properties of the support film 10 are enhanced. The overcoat layer was applied and formed on the barrier layer such that a solid content of the coating liquid was 2.0 g/m$^2$.

(3-2 Experiment Procedure)

As shown in FIG. 3, the prepared sample was cut in a size of 25 mm×120 mm to prepare an evaluation piece.

Figure 6:
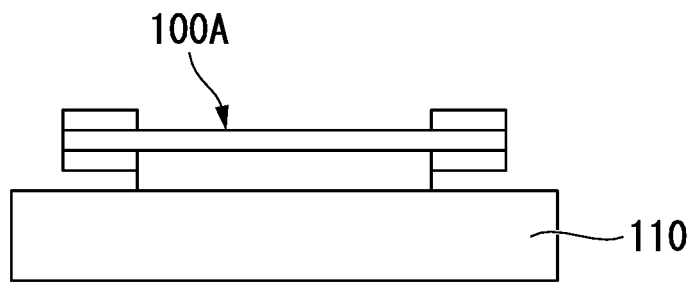
FIG. 6 is a view showing a procedure of an experiment examining elongation resistance of the barrier layer.

On a black acrylic plate in which scales were described, the sample piece was disposed such that the barrier layer 12 was on an upper side, and an end of the sample piece was fixed with an adhesive tape. Next, as shown in FIG. 6, while elongating the evaluation piece by 20% in a longitudinal direction, the other end of the evaluation piece 100A was fixed on the black acrylic plate 110 with the adhesive tape. A dimension (length) of a portion not covered with the adhesive tape in a longitudinal direction was 100 mm before elongation, and a dimension (length) of a portion not covered with the adhesive tape fixed onto the acrylic plate 110 by 20% of elongation was 120 mm.

After attachment of each evaluation piece 100A to the acrylic plate 110, as shown in FIG. 4, two droplets (approximately 0.08 g) of a plasticizer were dropped on the evaluation piece with a pipette in a state of 20% of elongation, and the dropped plasticizer was spread to a length of 50 mm on the evaluation piece 100A by using a cotton swab 112. As the plasticizer, isopropyl myristate (IPM) was used. The plasticizer was wiped after being left for 30 minutes and after being left for 3 hours at room temperature, and a swelling degree of the support was visually evaluated. As an index, presence or absence of wrinkles in the support 11 caused by swelling was used (2-stage evaluation: wrinkles due to swelling were not acknowledged: A, and wrinkles due to swelling were acknowledged: B).

In addition, in a state where the evaluation piece 100A was not elongated as well, plasticizer barrier properties were evaluated. The evaluation piece 100A was attached to the acrylic plate without being elongated, two droplets (approximately 0.08 g) of a plasticizer were dropped on the evaluation piece 100A with a pipette in a non-elongated state, and the dropped plasticizer was spread to a length of 50 mm on the evaluation piece 100A by using a cotton swab 112. As the plasticizer, isopropyl myristate (IPM) was used. The plasticizer was wiped after being left for 30 minutes and after being left for 3 hours at room temperature, and a swelling degree of the support 11 was visually evaluated. The index is the same as described above (2-stage evaluation: wrinkles due to swelling were not acknowledged: A, and wrinkles due to swelling were acknowledged: B).

(3-3 Result)

The result is shown in Table 3. In a reference (Control) in which glycerin was not added, it was determined that plasticizer barrier properties are present in a state where the evaluation piece 100A was not elongated. However, plasticizer barrier properties at the time of elongation of the evaluation piece 100A in the reference (Control) could not be determined. On the other hand, elongation resistance (permeability of plasticizer IPM at the time of elongation) started to be exhibited in the evaluation piece 100A by adding 5 wt % or greater of glycerin, and the effect of elongation resistance became remarkable at 10 wt % or greater. In Samples 1A, 2A, and 3A in which 5 wt % or greater of glycerin was added, from the result in which the elongation resistance was obtained, it is considered that plasticizer barrier properties are accordingly present in a non-elongated state as well (wrinkles due to swelling were not acknowledged: index A).

TABLE 3

| | SAMPLE CONSTITUTION COMPOSITION | | NON-ELONGATED | | PLASTICIZER (IPM) | |
|---|---|---|---|---|---|---|
| | SYNTHETIC MICA RATIO | GLYCERIN RATIO | PLASTICIZER (IPM) PERMEABILITY | | PERMEABILITY AT TIME OF 20% OF ELONGATION | |
| | (wt %) | (wt %) | 30 min. | 3 hr | 30 min. | 3 hr |
| CONTROL | 10 | — | A | A | B | B |
| SAMPLE 1A | 10 | 5 | (NOT MEASURED) | (NOT MEASURED) | A | B |
| | 10 | 10 | (NOT MEASURED) | (NOT MEASURED) | A | A |
| | 10 | 12.5 | (NOT MEASURED) | (NOT MEASURED) | A | A |
| SAMPLE 2A | 15 | 10 | (NOT MEASURED) | (NOT MEASURED) | A | A |
| | 15 | 12.5 | (NOT MEASURED) | (NOT MEASURED) | A | A |
| | 15 | 15 | (NOT MEASURED) | (NOT MEASURED) | A | A |
| SAMPLE 3A | 20 | 10 | (NOT MEASURED) | (NOT MEASURED) | A | B |
| | 20 | 12.5 | (NOT MEASURED) | (NOT MEASURED) | A | A |
| | 20 | 15 | (NOT MEASURED) | (NOT MEASURED) | A | A |

Next, an experiment result in which an influence of the barrier layer 12 on water vapor barrier properties due to a change of a ratio of a polyhydric alcohol and a layered inorganic compound was examined is shown.

(Experiment 4 Examination of Water Vapor Barrier Properties of Barrier Layer Due to Ratio of Additives)

(4-1 Sample Preparation)

Sample 1B containing 5 wt % of synthetic mica, Sample 2B containing 10 wt % of synthetic mica, Sample 3B containing 15 wt % of synthetic mica, and Sample 4B containing 20 wt % of synthetic mica were prepared. In Samples 3B and 4B, four types of variation samples obtained by changing a content ratio (wt %) of glycerin were prepared. Here, Sample 1B is a sample obtained by adding glycerin such that a proportion of glycerin is 10 wt % with respect to 5 wt % of synthetic mica and 95 wt % of polyurethane (a total of 100 wt %) to form a barrier layer 12. Sample 2B is a sample obtained by adding glycerin such that a proportion of glycerin is 10 wt % with respect to 10 wt % of synthetic mica and 90 wt % of polyurethane (a total of 100 wt %) to form a barrier layer 12.

Sample 3B is a sample obtained by adding glycerin such that a proportion of glycerin is 10 to 20 wt % with respect to 15 wt % of synthetic mica and 85 wt % of polyurethane (a total of 100 wt %) to form a barrier layer 12. Sample 4B is a sample obtained by adding glycerin such that a proportion of glycerin is 10 to 20 wt % with respect to 20 wt % of synthetic mica and 80 wt % of polyurethane (a total of 100 wt %) to form a barrier layer 12.

The barrier layer 12 was applied and formed on the support such that a solid content of a coating liquid was 2.0 g/m².

As the support 11, a polyether-based polyurethane support having a thickness of 20 μm was used. As the synthetic mica, a synthetic mica having an average particle diameter of 11 μm and an aspect ratio of 1000 or greater was used.

On the barrier layer, an overcoat layer constituted of 80 wt % of polyvinyl alcohol and 20 wt % of titanium lactate is formed. By using the overcoat layer along with the barrier layer 12, water vapor barrier properties of the support film 10 are enhanced. The overcoat layer was applied and formed on the barrier layer such that a solid content of the coating liquid was 2.0 g/m².

(4-2 Experiment Procedure)

An experiment procedure of water vapor barrier properties is the same as that of Experiment 1.

(4-3 Result)

Figure 7:
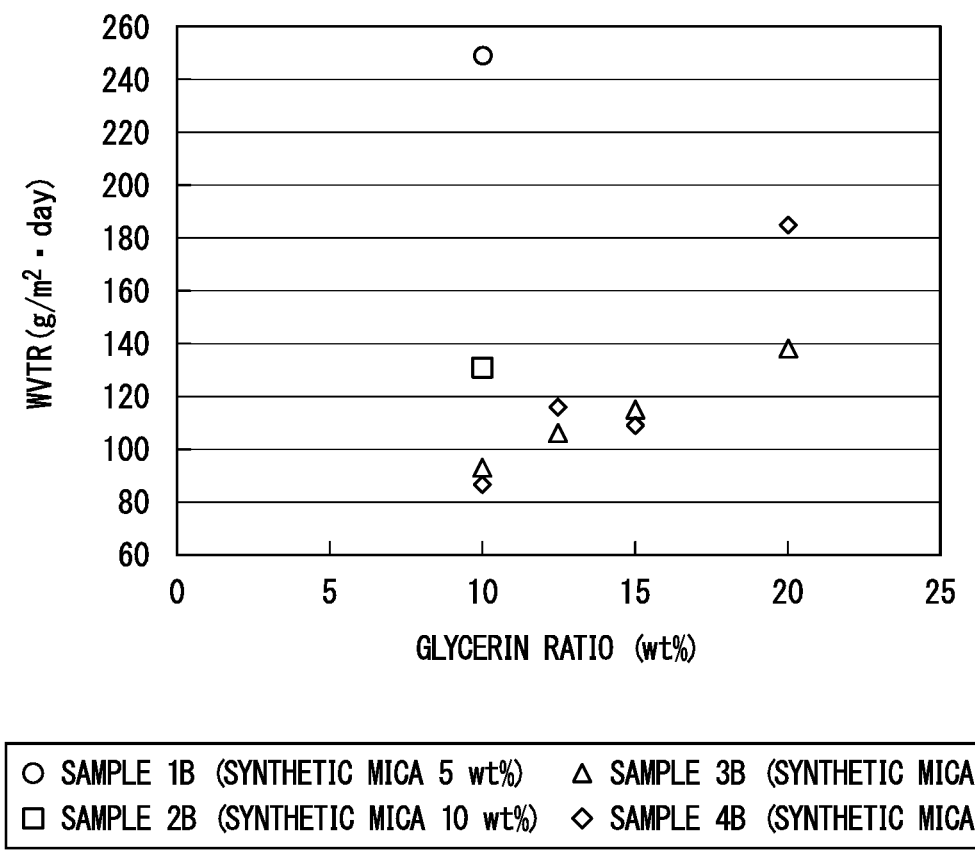
FIG. 7 is a graph showing a relationship between a ratio of the layered inorganic compound and a polyhydric alcohol and a water vapor permeability rate.

The result is shown in FIG. 7. From the results of water vapor permeability rates of Samples 1B, 2B, 3B, and 4B containing 10 wt % of glycerin, it was determined that the water vapor permeability rates (WVTR) were decreased by increasing the ratio of synthetic mica. However, even if the addition amount of the synthetic mica was increased such that the ratio of the synthetic mica was more than 15 wt %, a decrease of the water vapor permeability rate was not observed. It is considered that there is an upper limit in the addition amount of the synthetic mica that contributes to water vapor barrier properties.

In Samples 3B (15 wt % of synthetic mica) and 4B (20 wt % of synthetic mica), as a result of performing the experiment by changing the ratio of glycerin, it was determined that as the ratio of glycerin was increased, the water vapor permeability rate was increased.

From the results of Experiments 3 and 4, it is considered that if the addition amount of glycerin is increased, plasticizer barrier properties at the time of elongation are enhanced and water vapor barrier properties are decreased.

It is considered that the result of the water vapor permeability rate of Experiment 4 is lower than the results of the water vapor permeability rates of Experiments 1 and 2 since the water vapor permeability rate is affected by the overcoat layer formed on the barrier layer.

(Experiment 5 Examination in Relation to Layered Inorganic Compound/Water Vapor Barrier Properties)

(5-1 Sample Preparation)

Three types of samples of Sample 1C obtained by forming a barrier layer constituted of a single polyurethane layer not containing an layered inorganic compound on a support, Sample 2C obtained by forming a barrier layer in which 20 wt % of synthetic mica was added to 80 wt % of polyurethane on a support, and Sample 3C obtained by forming a barrier layer in which 20 wt % of montmorillonite was added to 80 wt % of polyurethane on a support were prepared.

The barrier layer according to Experiment 5 was applied and formed on the support such that a solid content of a coating liquid was 3.0 g/m².

As the support 11, a polyether-based polyurethane support having a thickness of 20 μm was used.

(5-2 Experiment Procedure)

An experiment procedure of water vapor barrier properties is the same as that of Experiment 1, and measurement of a water vapor permeability rate (WVTR) was performed by "testing methods for determination of the water vapor transmission rate of moisture-proof packaging materials (dish method)" of JIS-Z0208 (1976). Measurement was performed after standing still for 3 hours at 40° C. and 90% RH (relative humidity) by a dish method using a jig having an opening diameter of 80 mm, and the measurement value was converted into a moisture permeability amount for 24 hours per 1 m² to obtain a water vapor permeability rate.

(5-3 Result)

As the result in relation to water vapor barrier properties, the result shown in the following Table 4 was obtained.

TABLE 4

| | BARRIER LAYER CONSTITUTION | WATER VAPOR PERMEABILITY RATE (g/m² per day) |
|---|---|---|
| SAMPLE 1C | SINGLE POLYURETHANE LAYER | 504 |
| SAMPLE 2C | 80 wt % OF POLYURETHANE + 20 wt % OF SYNTHETIC MICA | 34 |
| SAMPLE 3C | 80 wt % OF POLYURETHANE + 20 wt % OF MONTMORILLONITE | 139 |

Even in a case where montmorillonite was used as a barrier layer material (layered inorganic compound), instead of synthetic mica, favorable water vapor barrier properties were shown.

Average particle diameters and aspect ratios of the synthetic mica and montmorillonite used in this Experiment 5 are as shown in Table 5.

TABLE 5

|  | AVERAGE PARTICLE DIAMETER (μm) | ASPECT RATIO |
|---|---|---|
| SYNTHETIC MICA | 11 | 1000< (ASPECT RATIO EXCEEDS 1000) |
| MONTMORILLONITE | 0.2 TO 0.5 | 460 |

It is considered that the synthetic mica has better water vapor barrier properties in a case of using synthetic mica than in a case of using montmorillonite since the water vapor barrier properties are affected by a difference in aspect ratios. In addition, it is considered that the water vapor barrier properties were also affected by the average particle diameter, and the one having a large average particle diameter had favorable water vapor barrier properties. It is considered that the labyrinthine effect due to a layered inorganic compound contributes to the result.

(Experiment 6 Examination in Relation to Layered Inorganic Compound/Plasticizer Barrier Properties)

(6-1 Sample Preparation)

Two types of samples of (1) Sample 1D obtained by forming a barrier layer on a support layer such that polyurethane is 80 wt % and montmorillonite is 20 wt % and (2) Sample 2D obtained by forming a barrier layer on a support such that polyurethane is 72 wt %, montmorillonite is 18 wt %, and glycerin is 10 wt % were prepared.

The barrier layer was applied and formed on the support such that a solid content of a coating liquid was 2.0 g/m².

In addition, an overcoat layer constituted of 80 wt % of polyurethane and 20 wt % of titanium lactate was formed on the barrier layer.

By using the overcoat layer along with the barrier layer 12, water vapor properties of the support film 10 are enhanced.

The overcoat layer was applied and formed on the barrier layer such that the solid content of the coating liquid was 2.0 g/m².

As the support 11, a polyether-based polyurethane support having a thickness of 20 μm was used.

Average particle diameters and aspect ratios of the montmorillonite used in this Experiment 6 are as shown in the following Table 6.

TABLE 6

|  | AVERAGE PARTICLE DIAMETER (μm) | ASPECT RATIO |
|---|---|---|
| MONTMORILLONITE | 0.2 TO 0.5 | 460 |

(6-2 Experiment Procedure)

In the plasticizer barrier evaluation, the prepared two types of samples 100 (Sample 1D, Sample 2D) were cut in a size of 25 mm×120 mm as shown in FIG. 3, and a sample piece 100A was disposed such that an overcoat layer was on an upper side on a black acrylic plate in which scales were described, and an end of the sample piece 100A was fixed with an adhesive tape.

Next, as shown in FIG. 6, while performing 10% and 20% of elongation with respect to the evaluation piece 100A in a longitudinal direction, the other end of the evaluation piece 100A was fixed on the black acrylic plate 110 with the adhesive tape. A dimension (length) of a portion not covered with the adhesive tape in the longitudinal direction was set to 100 mm.

After attachment of each evaluation piece 100A to the acrylic plate, as shown in FIG. 4, two droplets (approximately 0.08 g) of a plasticizer were dropped on the evaluation piece 100A with a pipette, and the dropped plasticizer was spread to a length of 50 mm on the evaluation piece 100A by using a cotton swab 112.

As the plasticizer, isopropyl myristate (IPM) was used.

The plasticizer was wiped after being left for 3 hours at room temperature, and a swelling degree of the support 11 was visually evaluated.

As an index, presence or absence of wrinkles in the support 11 caused by swelling was used (2-stage evaluation: wrinkles due to swelling were not acknowledged: A, and wrinkles due to swelling were acknowledged: B).

(6-3 Result)

The result shown in the following Table 7 was obtained.

TABLE 7

|  | BARRIER LAYER CONSTITUTION | PLASTICIZER BARRIER EVALUATION (10% ELONGATION) | PLASTICIZER BARRIER EVALUATION (20% ELONGATION) |
|---|---|---|---|
| SAMPLE 1D | POLYURETHANE + MONTMORILLONITE | A | B |
| SAMPLE 2D | POLYURETHANE + MONTMORILLONITE + GLYCERIN | A | A |

It was suggested that, even in a case where montmorillonite was used as a barrier layer material (layered inorganic compound), instead of synthetic mica, by adding glycerin to the barrier layer, plasticizer barrier properties are enhanced.

As described above, in the support film 10 according to the present embodiment, it is possible to enhance water vapor barrier properties by forming the barrier layer 12 by using an aromatic isocyanate-based polyurethane and a layered inorganic compound. In addition, it is possible to obtain plasticizer barrier properties by appropriately adding polyhydric alcohol such as glycerin.

Hereinabove, the embodiment of the present invention was described, but the technical scope of the present invention is not limited to the above embodiment, and it is possible to change the combination of the constituent elements of the embodiment within a range not departing from the present invention, and to add or delete various changes to each constituent element.

What is claimed is:

1. An adhesive tape material, wherein:
the adhesive tape material comprises a support film for the tape material,
the support film comprises a film-shaped support formed of polyurethane,
the support film further comprises a barrier layer formed on one surface of the support,
the adhesive tape material further comprises an overcoat layer comprising polyvinyl alcohol and titanium lactate on the barrier layer of the support film,
the barrier layer comprises:
an aromatic isocyanate-based polyurethane, the aromatic isocyanate-based polyurethane being a water-based polyurethane, which is made in aqueous conditions, formed of isocyanate including an aromatic group on a main chain or side chain and polyol;
a synthetic mica having an average particle diameter of 11 μm or more; and
a glycerin, and
the adhesive tape material further comprises an adhesive layer formed on the overcoat layer,
wherein an amount of the glycerin is within a range of from 10 wt % to 15 wt % with respect to a total amount (100 wt %) of the aromatic isocyanate-based polyurethane and the synthetic mica, and
wherein the total amount (100 wt %) is from 20 wt % of the synthetic mica and 80 wt % of the aromatic isocyanate-based polyurethane to 10 wt % of the synthetic mica and 90 wt % of the aromatic isocyanate-based polyurethane.

2. The adhesive tape material according to claim 1, wherein the adhesive layer comprises a plasticizer.

3. The adhesive tape material according to claim 2, wherein the adhesive layer is a mixture of the plasticizer and an adhesive base material.

4. The adhesive tape material according to claim 1 further comprising a release member formed on the adhesive layer.

5. The adhesive tape material according to claim 1, wherein the aspect ratio of the synthetic mica is 1000 or greater.

6. The adhesive tape material according to claim 1, wherein the synthetic mica comprises a plurality of flat structures, and the flat structures are stacked.

7. An adhesive tape material, wherein:
the adhesive tape material comprises a support film for the tape material,
the support film comprises a film-shaped support formed of polyurethane,
the support film further comprises a barrier layer formed on one surface of the support,
the adhesive tape material further comprises an overcoat layer comprises polyvinyl alcohol and titanium lactate on the barrier layer of the support film,
the barrier layer consisting essentially of:
an aromatic isocyanate-based polyurethane, the aromatic isocyanate-based polyurethane being a water-based polyurethane, which is made in aqueous conditions, formed of isocyanate including an aromatic group on a main chain or side chain and polyol;
a synthetic mica having an average particle diameter of 11 μm or more; and
a glycerin, and
the adhesive tape material further comprises an adhesive layer formed on the overcoat layer,
wherein an aspect ratio of the synthetic mica is 1000 or greater,
wherein the synthetic mica comprises a plurality of flat structures, and the flat structures are stacked,
wherein an amount of the glycerin is within a range of from 10 wt % to 15 wt % with respect to a total amount (100 wt %) of the aromatic isocyanate-based polyurethane and the synthetic mica,
wherein the total amount (100 wt %) is from 20 wt % of the synthetic mica and 80 wt % of the aromatic isocyanate-based polyurethane to 10 wt % of the synthetic mica and 90 wt % of the aromatic isocyanate-based polyurethane,
wherein a water vapor permeability rate of a first support film constituted of the support film and the overcoat layer is smaller than a water vapor permeability rate of the support film, and
wherein the adhesive layer comprises a drug and an absorption rate of the drug into a skin is configured to be enhanced by an effect of occlusive dressing therapy (ODT).

8. The adhesive tape material according to claim 7, wherein the adhesive layer comprises a plasticizer.

9. The adhesive tape material according to claim 7, wherein the adhesive layer is a mixture of the plasticizer and an adhesive base material.

10. The adhesive tape material according to claim 7, further comprising a release member formed on the adhesive layer.

* * * * *